US008939993B1

(12) United States Patent
Thenuwara et al.

(10) Patent No.: US 8,939,993 B1

(45) Date of Patent: *Jan. 27, 2015

(54) PRE-CURVED ELECTRODE ARRAY LOADING TOOLS

(75) Inventors: Chuladatta Thenuwara, Castaic, CA (US); William G. Orinski, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 1626 days.

This patent is subject to a terminal disclaimer.

(21) Appl. No.: 12/485,427

(22) Filed: Jun. 16, 2009

Related U.S. Application Data

(63) Continuation-in-part of application No. 11/933,861, filed on Nov. 1, 2007.

(60) Provisional application No. 60/858,087, filed on Nov. 8, 2006, provisional application No. 60/925,526, filed on Apr. 20, 2007.

(51) Int. Cl.
*A61B 19/00* (2006.01)

(52) U.S. Cl.
USPC ........... 606/129; 604/174; 607/126; 607/127; 607/137; 600/373; 600/393

(58) Field of Classification Search
USPC ............ 606/129, 174; 607/91, 126, 127, 137; 604/373, 393; 600/373, 393
See application file for complete search history.

(56) References Cited

U.S. PATENT DOCUMENTS 4,819,647 A 4/1989 Byers et al.
4,898,183 A 2/1990 Kuzma
5,314,411 A * 5/1994 Bierman et al. .............. 604/174
5,443,493 A 8/1995 Byers et al.
5,667,514 A 9/1997 Heller
6,070,105 A 5/2000 Kuzma
6,125,302 A 9/2000 Kuzma
6,129,753 A 10/2000 Kuzma (Continued)

FOREIGN PATENT DOCUMENTS

EP 0109304 5/1984
EP 0328597 8/1989

(Continued)

OTHER PUBLICATIONS

Non-Final Office Action received in U.S. Appl. No. 11/933,861 dated Oct. 1, 2010.

(Continued)

*Primary Examiner* — Victor Nguyen

*Assistant Examiner* — Kevin Everage

(74) *Attorney, Agent, or Firm* — ALG Intellectual Property, LLC

(57) ABSTRACT

Exemplary systems for loading a pre-curved electrode array onto a stylet include a loading tool and a stylet retainer. The loading tool includes a docking assembly comprising a plurality of wing members that form a receptacle configured to receive a proximal portion of the stylet, a channel assembly comprising a channel configured to receive and allow passage therethrough of the pre-curved electrode array, the channel further configured to receive a distal portion of the stylet, and a connecting member configured to connect the channel assembly to the docking assembly. The stylet retainer is configured to couple to the loading tool to retain the stylet within the loading tool while the pre-curved electrode array is loaded onto the stylet. Corresponding methods are also described.

13 Claims, 17 Drawing Sheets

716 1100 708 112 900 308 400 1110 710 700

(56) References Cited

U.S. PATENT DOCUMENTS

| | | | |
|---|---|---|---|
| 6,149,657 | A | 11/2000 | Kuzma |
| 6,195,586 | B1 | 2/2001 | Kuzma |
| 6,219,580 | B1 | 4/2001 | Faltys et al. |
| 6,272,382 | B1 | 8/2001 | Faltys et al. |
| 6,308,101 | B1 | 10/2001 | Faltys et al. |
| 6,421,569 | B1 | 7/2002 | Treaba et al. |
| 6,604,283 | B1 | 8/2003 | Kuzma |
| 6,968,238 | B1 | 11/2005 | Kuzma |
| 7,050,858 | B1 | 5/2006 | Kuzma et al. |
| 7,063,708 | B2 | 6/2006 | Gibson et al. |
| 7,269,461 | B2 | 9/2007 | Dadd et al. |
| 2002/0111634 | A1 | 8/2002 | Stoianovici et al. |
| 2003/0093139 | A1 | 5/2003 | Gibson et al. |
| 2004/0243177 | A1 | 12/2004 | Svehla et al. |
| 2005/0251237 | A1 | 11/2005 | Kuzma et al. |
| 2005/0267555 | A1 | 12/2005 | Marnfeldt et al. |
| 2006/0058861 | A1 | 3/2006 | Gibson et al. |
| 2006/0241723 | A1 | 10/2006 | Dadd et al. |
| 2008/0004684 | A1 | 1/2008 | Dadd et al. |
| 2008/0109011 | A1 | 5/2008 | Thenuwara et al. |
| 2008/0294174 | A1 | 11/2008 | Bardsley et al. |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1476104 | 11/2004 |
| WO | WO-8900870 | 2/1989 |
| WO | WO-9324058 | 12/1993 |
| WO | WO-9720530 | 6/1997 |
| WO | WO-00/71063 | 11/2000 |
| WO | WO-0230507 | 4/2002 |
| WO | WO-0232498 | 4/2002 |
| WO | WO-02074211 | 9/2002 |
| WO | WO-03070133 | 8/2003 |
| WO | WO-2004012809 | 2/2004 |
| WO | WO-2008/057989 | 5/2008 |

OTHER PUBLICATIONS

Non-Final Office Action received in U.S. Appl. No. 11/933,861 dated Apr. 14, 2010.

International Search Report and Written Opinion received in International Application No. PCT/US2011/035541, dated Oct. 7, 2011.

International Search Report and Written Opinion received in International Application No. PCT/US2011/035539, dated Dec. 29, 2011.

Final Office Action received in U.S. Appl. No. 11/933,861, dated Apr. 28, 2011.

International Search Report and Written Opinion received in International Application No. PCT/US2007/083428.

* cited by examiner

PRE-CURVED ELECTRODE ARRAY LOADING TOOLS

RELATED APPLICATIONS

The present application is a continuation-in-part application of U.S. patent application Ser. No. 11/933,861 by Chuladatta Thenuwara et al., filed Nov. 1, 2007, which application claims the benefit of U.S. Provisional Patent Application No. 60/858,087 by Chuladatta Thenuwara et al., filed Nov. 8, 2006, and to U.S. Provisional Patent Application No. 60/925,526 by Chuladatta Thenuwara et al., filed Apr. 20, 2007. Each of these applications is incorporated herein by reference in their respective entireties.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an array of electrodes may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to auditory nerves within the cochlea via one or more of the electrodes.

The electrode array is often implanted within the scala tympani, one of the three parallel ducts that make up the spiral-shaped cochlea. Electrode arrays that are implanted in the scala tympani typically include a thin, elongate, and flexible carrier containing several longitudinally disposed and separately connected stimulating electrode contacts. Such an electrode array is pushed into the scala tympani duct to a depth of about 18-25 mm via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various pre-curved electrode arrays have been developed that have spiral-shaped resilient carriers to better conform to the shape of the scala tympani and/or other auditory structures.

However, many pre-curved electrode arrays have to first be loaded onto a straight stylet of an insertion tool before they can be inserted into the cochlea. Current methods of loading pre-curved electrode arrays onto straight stylets are cumbersome and often result in damage to the electrode arrays as they are loaded onto the stylets.

SUMMARY

Exemplary systems for loading a pre-curved electrode array onto a stylet include a loading tool and a stylet retainer. The loading tool includes a docking assembly comprising a plurality of wing members that form a receptacle configured to receive a proximal portion of the stylet, a channel assembly comprising a channel configured to receive and allow passage therethrough of the pre-curved electrode array, the channel further configured to receive a distal portion of the stylet, and a connecting member configured to connect the channel assembly to the docking assembly. The stylet retainer is configured to couple to the loading tool to retain the stylet within the loading tool while the pre-curved electrode array is loaded onto the stylet.

Exemplary methods of loading a pre-curved electrode array onto a stylet include providing a loading tool having a docking assembly and a channel assembly, the docking assembly comprising a plurality of wing members that form a receptacle, the channel assembly comprising a channel, inserting a distal portion of the stylet into a lumen of a proximal portion of the electrode array, placing the distal portion of the stylet and the proximal portion of the pre-curved electrode array into the channel and a proximal portion of the stylet into the receptacle, coupling a stylet retainer to the loading tool to retain the distal portion of the stylet within the channel and the proximal portion of the stylet within the receptacle, and advancing the pre-curved electrode array through the channel onto the stylet.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Exemplary systems and methods for loading a pre-curved electrode array onto a stylet are described herein. In some examples, a loading tool includes a docking assembly comprising a plurality of wing members that form a receptacle configured to receive a proximal portion of the stylet, a channel assembly comprising a channel configured to receive and allow passage therethrough of the pre-curved electrode array, the channel further configured to receive a distal portion of the stylet, and a connecting member configured to connect the channel assembly to the docking assembly and maintain a distance therebetween. The stylet retainer is configured to couple to the loading tool to retain the stylet within the loading tool while the pre-curved electrode array is loaded onto the stylet.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
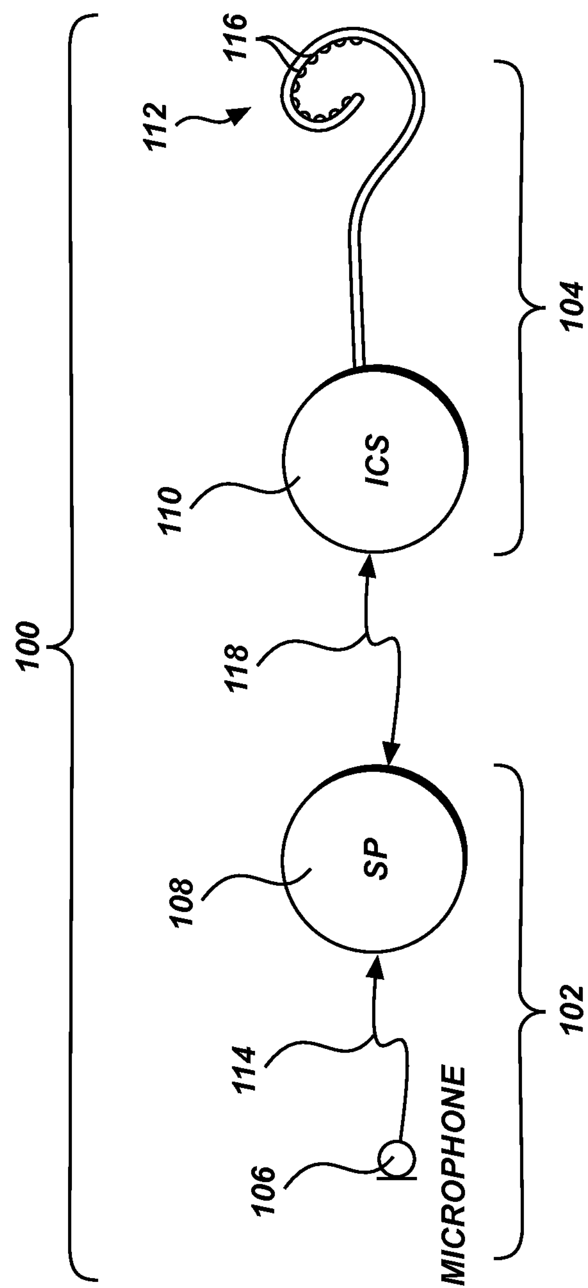
FIG. 1 illustrates an exemplary cochlear implant system according to principles described herein.

FIG. 1 illustrates an exemplary cochlear implant system 100 that may be used in accordance with the present systems and methods. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties.

The cochlear implant system 100 of FIG. 1 includes a sound processor portion 102 and a cochlear stimulation portion 104. The sound processor portion 102 may include a microphone 106, a sound processor (SP) 108, and/or additional components as may serve a particular application. The cochlear stimulation portion 104 may include an implantable cochlear stimulator (ICS) 110, a pre-curved electrode array 112, and/or additional components as may serve a particular application. The illustrated components within sound processor portion 102 and cochlear stimulation portion 104 will be described in more detail below.

Microphone 106 is configured to sense acoustic signals and convert the sensed signals to corresponding electrical signals. The electrical signals are sent from microphone 106 to sound processor 108 via a communication link 114. Alternatively, microphone 106 may be connected directly to, or integrated with, sound processor 108. Sound processor 108 processes these converted acoustic signals in accordance with a selected signal processing strategy to generate appropriate stimulation parameters for controlling implantable cochlear stimulator 110. These parameters may specify or define the polarity, magnitude, location (i.e., which electrode pair or electrode group receive the stimulation current), and timing (i.e., when the stimulation current is to be applied to a particular electrode pair) of the electrical stimulation pulses that are generated by implantable cochlear stimulator 110.

The pre-curved electrode array 112 (also referred to herein as simply "electrode array 112") of FIG. 1 is configured to be inserted within a duct of the cochlea. As shown in FIG. 1, electrode array 112 includes a multiplicity of electrodes 116, e.g., sixteen electrodes, spaced along its length. It will be understood, however, that any number of electrodes 116 may be included within electrode array 112. Electrode array 112 will be described in more detail below. One or more components within implantable cochlear stimulator 110 are configured to generate stimulation current via selected pairs or groups of individual electrodes 116 in accordance with a specified stimulation pattern defined by sound processor 108.

Implantable cochlear stimulator 110 and sound processor 108 may be electronically connected via a suitable data or communication link 118. It will be understood that the data communication link 118 may include a bi-directional communication link and/or one or more dedicated uni-directional communication links.

In some examples, sound processor 108 and microphone 106 comprise an external portion of cochlear implant system 100 and implantable cochlear stimulator 110 and electrode array 112 comprise an implantable portion of system 100 that is implanted within a patient's body. In alternative embodiments, one or more portions of sound processor 108 are included within the implantable portion of the cochlear implant system 100.

The external and implantable portions of the cochlear implant system 100 may each include one or more coils configured to transmit and receive power and/or control signals via communication link 118. For example, the external portion of cochlear implant system 100 may include an external coil (not shown) and the implantable portion of cochlear implant system 100 may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of cochlear implant system 100. It will be noted that, in some embodiments, both sound processor 108 and implantable cochlear stimulator 110 may be implanted within the patient, either in the same housing or in separate housings. If sound processor 108 and implantable cochlear stimulator 110 are in the same housing, communication link 118 may be realized with a direct wire connection within such housing. If sound processor 108 and implantable cochlear stimulator 110 are in separate housings, communication link 118 may include one or more inductive links, for example.

Figure 2:
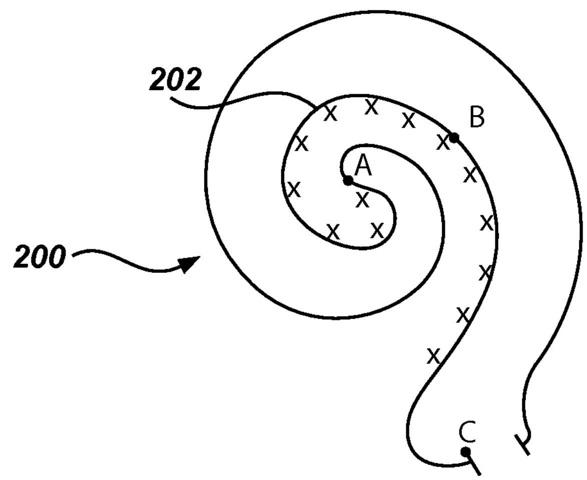
FIG. 2 illustrates a schematic structure of human cochlea according to principles described herein.

Referring to FIG. 2, there is shown a schematic structure of a human cochlea 200. The section of the cochlea 200 from point A to point B, i.e., section AB, has a spiral shape. In contrast, the section from point B to point C, i.e., section BC, is almost straight. The area of stimulation, i.e., the location of the spiral ganglion cells, is marked with X's and is separated from the duct of the cochlea 200 by the modiolar wall 202. As described previously, it is often desirable for electrodes 116 to be positioned in close proximity to the spiral ganglion cells.

Figure 3:
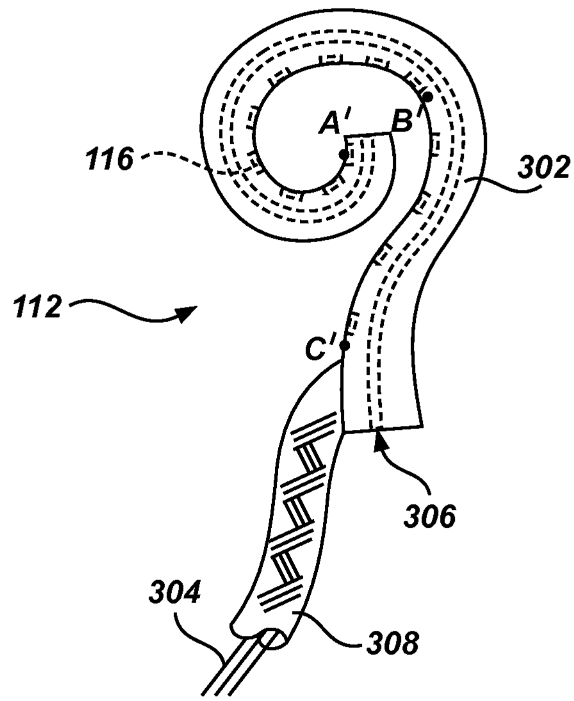
FIG. 3 illustrates an exemplary pre-curved electrode array according to principles described herein.

To facilitate proper positioning of electrodes 116, a pre-curved electrode array 112 is provided as shown in FIG. 3. The electrode array 112 may be substantially as shown and described in U.S. Pat. Nos. 4,819,647; 6,129,753; or 6,604,283, each of which is incorporated herein by reference in its respective entirety.

As shown in FIG. 3, electrode array 112 has the same general curvature as that of the cochlea 200. In some examples, electrode array 112 includes an elongate flexible carrier 302 having an array of electrode contacts 116 connected to corresponding insulated wires 304. Elongate flexible carrier 302 may be made out of any suitable material such as, but not limited to, silicone rubber or plastic, and has a hole or lumen 306 passing therethrough. In some examples, carrier 302 is constructed so as to have a built-in bias or memory force which forces carrier 302 to naturally assume the spiral or curved shape shown in FIG. 3. In addition, the material of the carrier 302 may be configured to allow carrier 302 to be straightened when loaded on a stylet. Once inserted within the duct of the cochlea 200, the memory force of carrier 302 forces carrier 302 to return to the desired curvature, e.g., as shown in FIG. 3.

As shown in FIG. 3, a proximal end of carrier 302 is coupled to a lead body 308 through which wires 304 continue and connect to implantable cochlear stimulator 110. Implantable cochlear stimulator 110 is thus able to make electrical connection with each of the electrode contacts 116 through one or more of wires 304.

In some examples, the electrode contacts 116 of electrode array 112 are configured to be positioned along the medial electrode wall following the line between points A', B' and C'. This line, as shown in FIG. 3, is along a portion of the curve or spiral that is generally concave.

Figure 4:
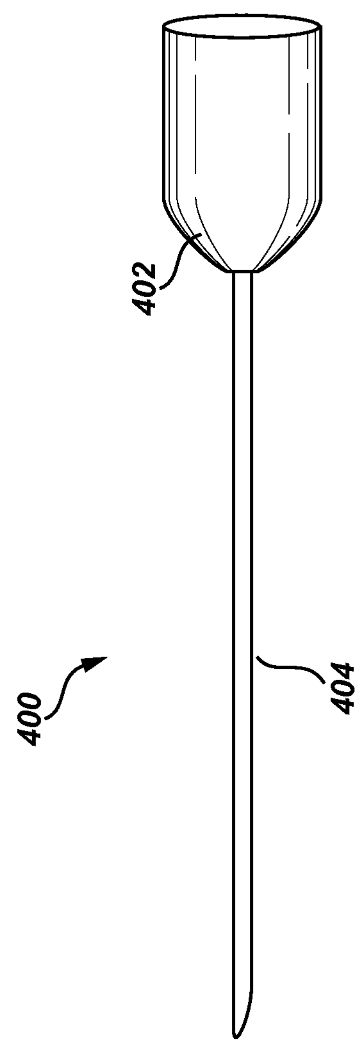
FIG. 4 is a perspective view of an exemplary stylet that may be used to insert a pre-curved electrode array into a duct of the cochlea according to principles described herein.

As mentioned, pre-curved electrode array 112 often has to be loaded onto a substantially straight stylet before it can be implanted within a duct of the cochlea. FIG. 4 is a perspective view of an exemplary stylet 400 that may be used in accordance with the systems and methods described herein. As shown in FIG. 4, stylet 400 may include a handle member 402 coupled to a substantially straight member 404. Handle member 402 may be of a dimension to accommodate manual handling thereof and/or attachment of forceps or other tools thereto. Substantially straight member 404, as will be described in more detail below, may be configured to be at least partially inserted into a lumen of pre-curved electrode array 112. Stylet 400 shown in FIG. 4 is a stand-alone stylet for illustrative purposes only. It will be recognized that stylet 400 may alternatively be coupled to or a part of an insertion tool.

Stylet 400 may be made out of any suitable material with sufficient stiffness so as to facilitate entry into the cochlea. For example, stylet 400 may be made out of a metal, a metal alloy, a hard plastic, or any other suitable material.

Figure 5:
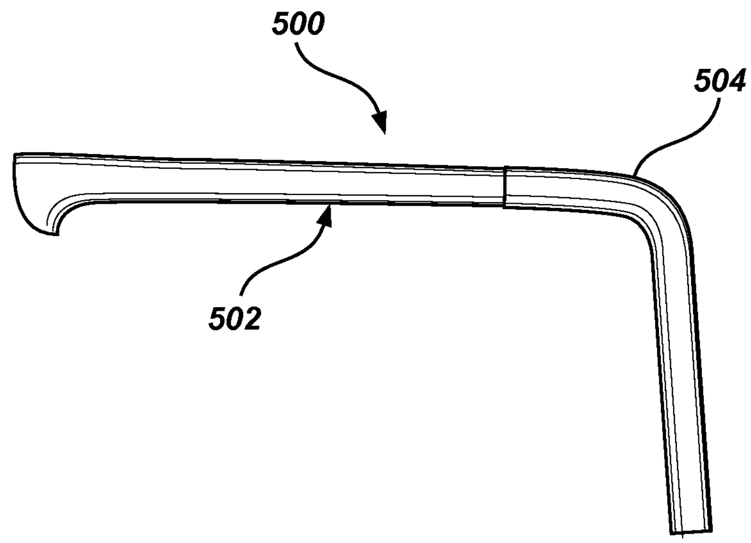
FIG. 5 illustrates an exemplary loading tool that is often used to load a pre-curved array onto the stylet of an insertion tool according to principles described herein.

FIG. 5 illustrates an exemplary loading tool 500 that is often used to load the pre-curved electrode array 112 onto the stylet 400. As shown in FIG. 5, loading tool 500 includes a tube 502 with an elongate hollow lumen extending therethrough. Tube 502 is coupled at one of its ends to a bent handle 504.

Tube 502 includes an opening at both of its ends to allow passage therethrough of the electrode array 112 and stylet 400. Tube 502 has a length at least as long as the length of pre-curved electrode array 112 in a straightened state.

In some examples, electrode array 112 is inserted into the lumen of tube 502 prior to being loaded onto stylet 400. Ideally, the diameter of the lumen is such that electrode array 112 becomes substantially straight as it is inserted therein. Stylet 400 may then be inserted into lumen 306 of electrode array 112.

Figure 6:
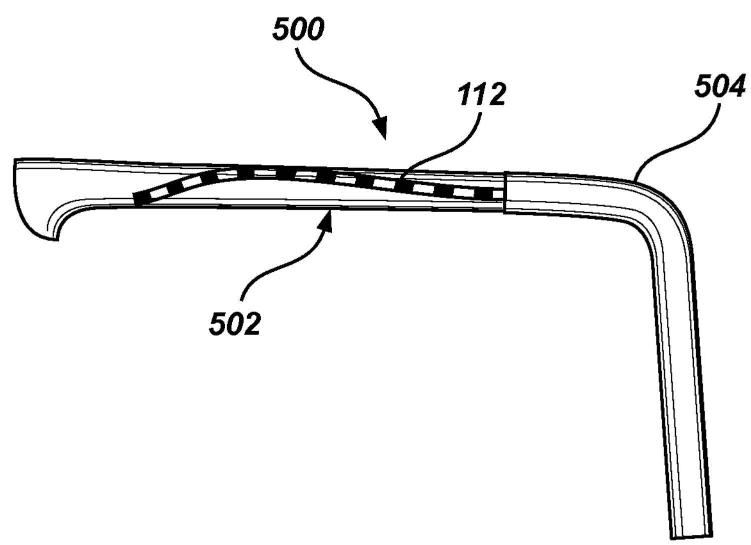
FIG. 6 shows an exemplary pre-curved electrode array that has been inserted into the lumen of the loading tool of FIG. 5 according to principles described herein.

However, because electrode array 112 has a tendency to assume its pre-curved shaped, electrode array 112 is often not completely straight within the lumen of the tube 502. For example, FIG. 6 shows an exemplary pre-curved electrode array 112 that has been inserted into the lumen of loading tool 500. As shown in FIG. 6, electrode array 112 has a wave-type shape and is not completely straight. Hence, stylet 400 may puncture the wall of the electrode array from within lumen 306 or otherwise cause damage to electrode array 112 when inserted into the electrode array's lumen 306.

Hence, the present systems and methods provide a loading tool that does not require electrode array 112 to be completely straightened prior to being loaded onto a stylet 400.

Figure 7A:
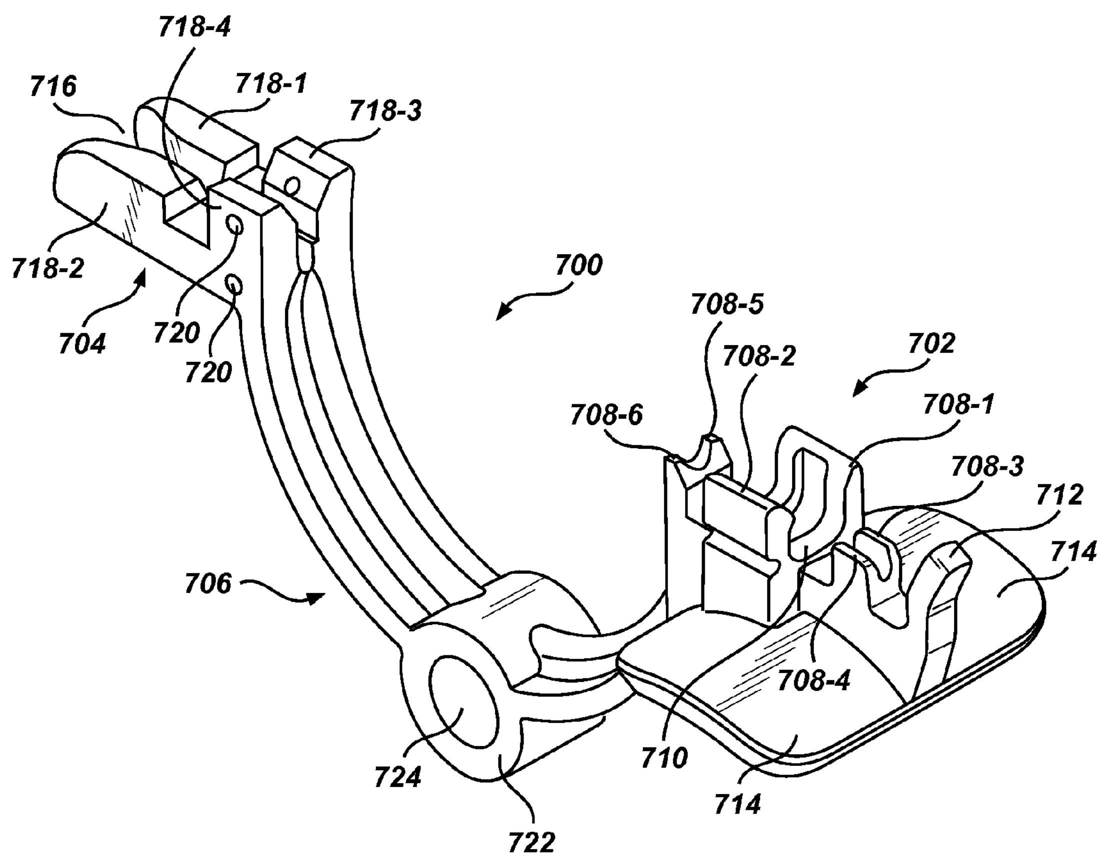
FIG. 7A is a perspective view of a loading tool configured to facilitate loading of a pre-curved electrode array onto a stylet according to principles described herein.
Figure 7B:
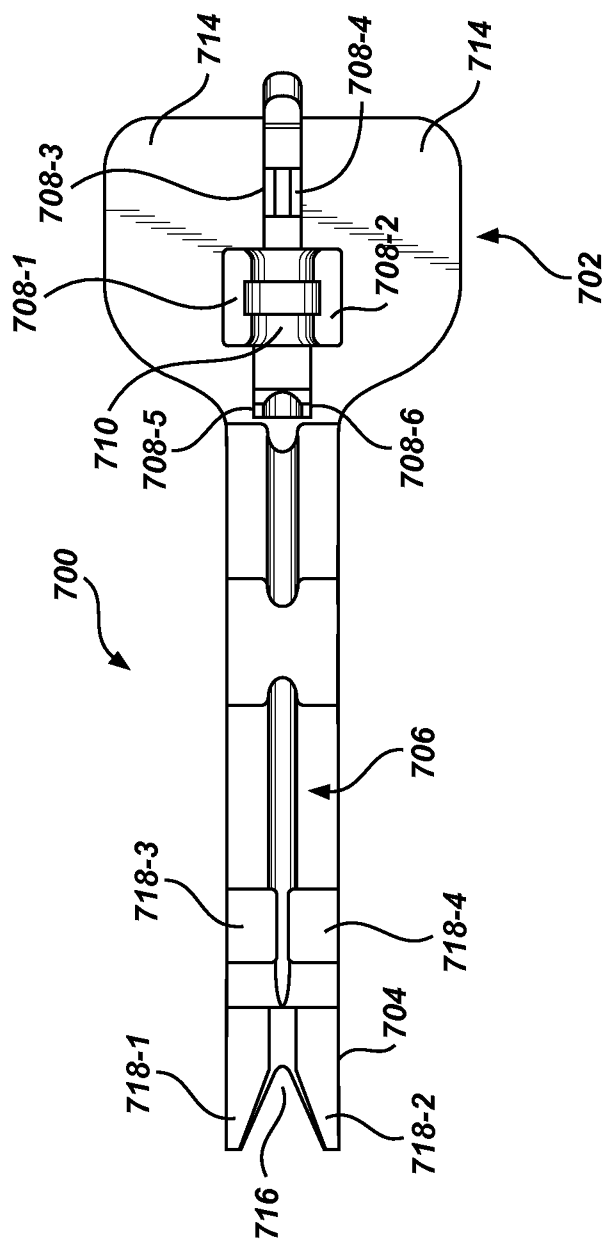
FIG. 7B is a top view of the loading tool shown in FIG. 7A according to principles described herein.

FIG. 7A is a perspective view of a loading tool 700 configured to facilitate loading of a pre-curved electrode array 112 onto a stylet 400. FIG. 7B is a top view of the loading tool 700 shown in FIG. 7A. As will be described in more detail below, loading tool 700 allows a surgeon or other user thereof to load a pre-curved electrode array 112 onto a stylet 400 without first having to completely straighten pre-curved electrode array 112.

As shown in FIG. 7A, the loading tool 700 may include a docking assembly 702, a channel assembly 704, and a connecting member 706 extending therebetween. Each of these components will be described in more detail below. It will be recognized that loading tool 700 shown in FIGS. 7A-7B is merely illustrative of the many different loading tools that may be used in connection with the methods and systems described herein. An alternative loading tool that may be used will be described in more detail below.

Docking assembly 702, as shown in FIG. 7A, is located at a proximal end of loading tool 700 and includes a plurality of wing members 708-1 through 708-6, collectively referred herein as "wing members 708." At least a subset of wing members 708 may be configured to form or define a receptacle 710. Receptacle 710 may be configured to receive a proximal portion of stylet 400, as will be described in more detail below. Docking assembly 702 may further include a backstop member 712 configured to facilitate proper placement of stylet 400 within receptacle 710.

In some examples, the docking assembly 702 may also include one or more flanges 714 configured to facilitate handling of loading tool 700. Flanges 714 may have any suitable shape and size as may serve a particular application. In some examples, one or more of the flanges 714 may include laser etched wording or other identification marks.

As shown in FIGS. 7A-7B, channel assembly 704 includes a channel 716 extending therethrough. As will be described in more detail below, pre-curved electrode array 112 may be placed within and advanced (e.g., pulled) through channel 716 to load pre-curved electrode array 112 onto stylet 400. Hence, channel 716 may have any suitable width and depth that allows for placement of pre-curved electrode 112 therein. In some examples, a bottom surface of channel 716 at a distal end is curved or rounded so as to facilitate easier passage of pre-curved electrode 112 therethrough.

Channel 716 may be formed or defined by a plurality of wall members 718-1 through 718-4, collectively referred to herein as "wall members 718." Wall members 718 may be configured to prevent electrode array 112 from moving laterally within channel 716. As seen more easily in FIG. 7B, the distal ends of the wall members 718-1 and 718-2 may be angled or tapered away from the distal end of the channel 716. In this manner, wall members 718-1 and 718-2 may be further configured to guide electrode array 112 into channel 716 as electrode array 112 is being pulled therethrough.

In some examples, wall members 718-3 and 718-4 may include a plurality of holes 720 extending laterally therethrough. As will be described in more detail below, a retainer clip may be inserted into holes 720 to secure stylet 400 within channel 716.

Channel 716, as more readily seen in FIG. 7B, is aligned linearly with receptacle 710 of docking assembly 702. In this manner, as will be described in more detail below, a distal portion of stylet 400 may be placed within channel 716 at substantially the same time that a proximal portion of stylet 400 is placed within receptacle 710.

Connecting member 706, as shown in FIGS. 7A-7B, is configured to connect docking assembly 702 to channel assembly 704. It will be recognized that connecting member 706 may have any alternative shape as may serve a particular application. An alternative shape of connecting member 706 will be described in more detail below.

In some examples, connecting member 706 includes a finger grip 722 configured to facilitate easier handling thereof. The finger grip 722 may include a lumen 724 extending therethrough, as shown in FIG. 7A. Additionally or alternatively, the finger grip 722 may include any other structure as may serve a particular application.

In some examples, one or more of the components of loading tool 700 may be made out of any biocompatible material as may serve a particular application. For example, loading tool 700 may be made out of any suitable metal or a plastic (e.g., polysulfone). In some examples, loading tool 700 is made out of a material that can be sterilized.

In some examples, loading tool 700 may be made out of a single mold. In this manner, loading tool 700 may be manufactured using any suitable plastic injection molding process. Alternatively, as will be described in more detail below, the components of loading tool 700 may be coupled one to another using any other method.

Figure 8A:
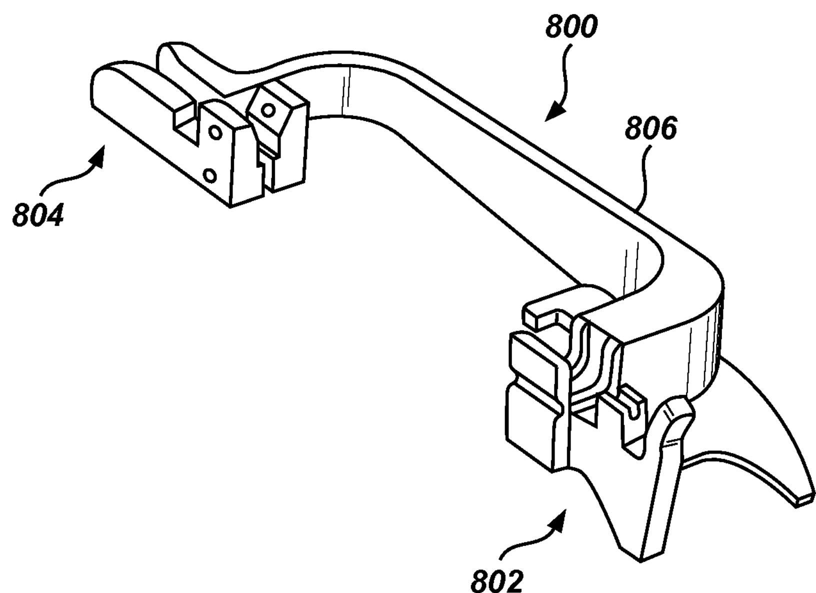
FIG. 8A is a perspective view of another loading tool according to principles described herein.
Figure 8B:
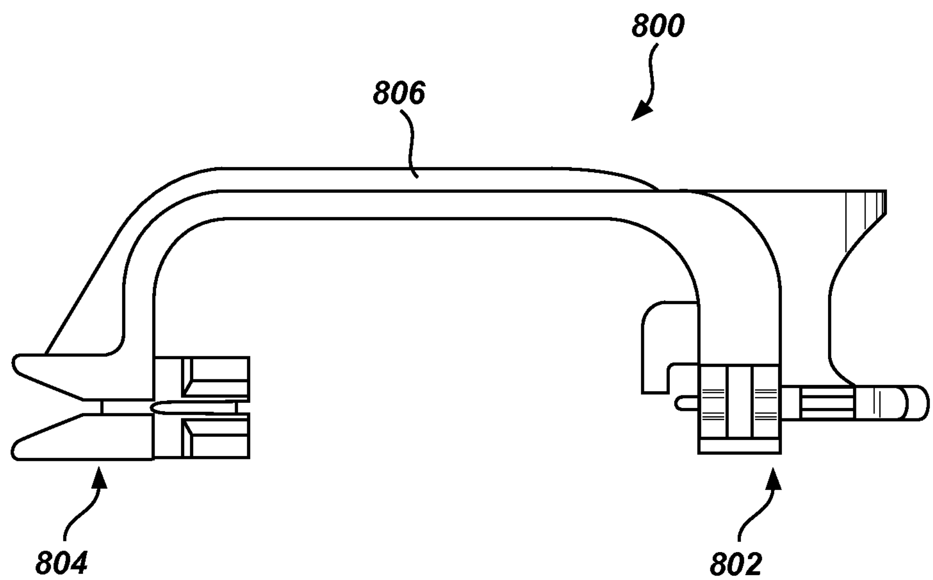
FIG. 8B is a top view of the loading tool shown in FIG. 8A according to principles described herein.

FIG. 8A is a perspective view of an alternative loading tool 800 that may be used in connection with the systems and methods described herein. FIG. 8B is a top view of the loading tool 800 shown in FIG. 8A. Loading tool 800 is similar to loading tool 700 in that loading tool 800 includes a docking assembly 802, a channel assembly 804, and a connecting member 806 extending therebetween. However, as shown in FIGS. 8A-8B, connecting member 806 may include a C-shaped member extending laterally from docking member 802 such that docking assembly 802, channel assembly 804, and connecting member 806 are located substantially in the same plane.

It will be recognized that either loading tool 700 or 800 may be used in accordance with the systems described herein. Hence, references made herein and in the appended claims to a "loading tool" and/or any component thereof may refer to loading tool 700, loading tool 800, and/or any component thereof.

Figure 9A:
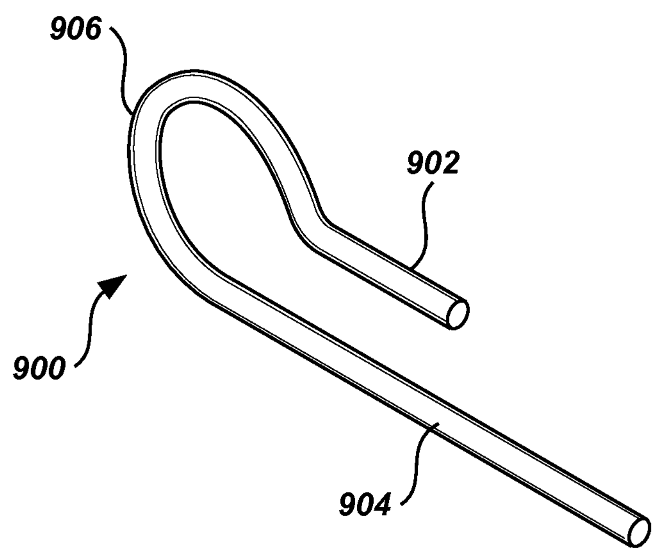
FIG. 9A is a perspective view of an exemplary retainer clip according to principles described herein.
Figure 9B:
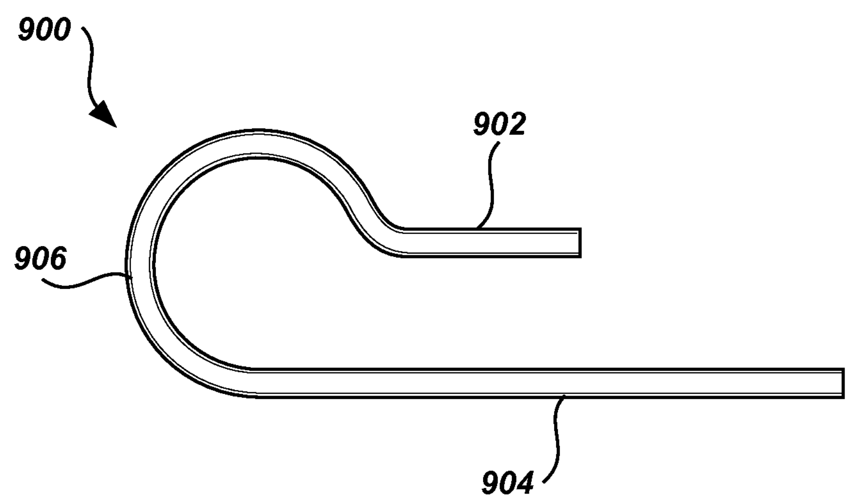
FIG. 9B is a side view of the retainer clip of FIG. 9A according to principles described herein.

In some examples, a retainer clip or other securing device or mechanism may be provided to secure stylet 400 within channel 716. FIG. 9A is a perspective view of an exemplary retainer clip 900 and FIG. 9B is a side view of the retainer clip 900 of FIG. 9A. As shown in FIGS. 9A-9B, retainer clip 900 may include two substantially straight members 902 and 904 with a curved member 906 positioned therebetween. The straight members 902 and 904 are configured to be inserted into corresponding holes located within loading tool 700. In some examples, as will be described in more detail below, the bottom straight member 904 is longer than the top straight member 902. The curved member 900 may be gripped by a surgeon or other user. It will be recognized that the retainer clip 900 shown in FIGS. 9A-9B is merely exemplary and that any other type of retainer clip or securing device may additionally or alternatively be used to secure stylet 400 within channel 716.

Figure 10A:
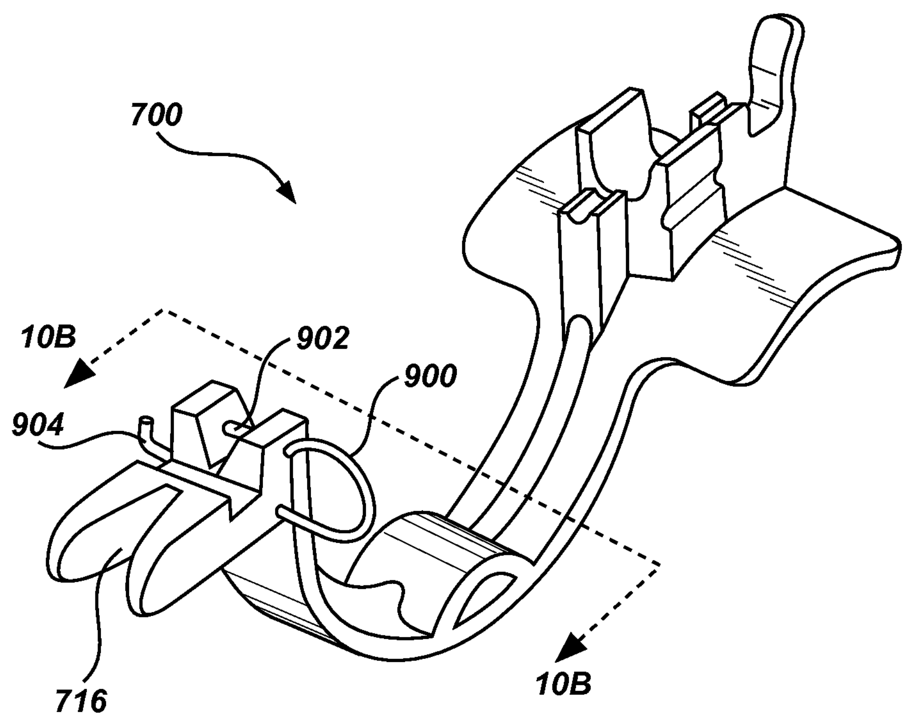
FIG. 10A is a perspective view of the retainer clip inserted into a channel assembly of a loading tool according to principles described herein.
Figure 10B:
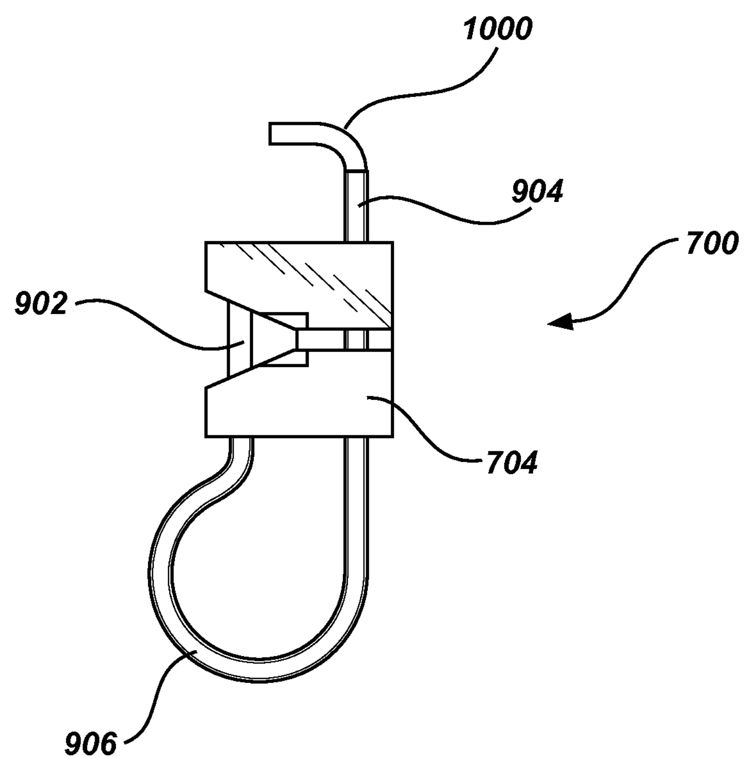
FIG. 10B is a cross sectional view of the retainer clip inserted into the channel assembly taken along the perspective line indicated in FIG. 10A according to principles described herein.

FIG. 10A is a perspective view of retainer clip 900 inserted into channel assembly 704 of loading tool 700. FIG. 10B is a cross sectional view of retainer clip 900 inserted into channel assembly 704 taken along the perspective line indicated in FIG. 10A. As shown in FIGS. 10A-10B, the straight members 902 and 904 of retainer clip 900 are inserted into corresponding holes 720 of channel assembly 704. Holes 720 are positioned such that top member 902 is above channel 716 and bottom member 904 is beneath channel 716.

As shown in FIGS. 10A-10B, a distal end 1000 of bottom straight member 904 may be bent at an angle after it is inserted within channel assembly 704. In this manner, retainer clip 900 may be prevented from completely coming out of channel assembly 704 if pulled too far.

Hence, to place and secure stylet 400 within channel 716 of channel assembly 704, retainer clip 900 is first disengaged or pulled away from channel assembly 704 until the shorter top member 902 of retainer clip 900 does not cover the channel 716. Stylet 400 may then be placed within channel 716. Retainer clip 900 may then be engaged with (e.g., pushed through) holes 720 of channel assembly 704 until the top member 902 covers a portion of stylet 400 that is within the channel 716.

Figure 11A:
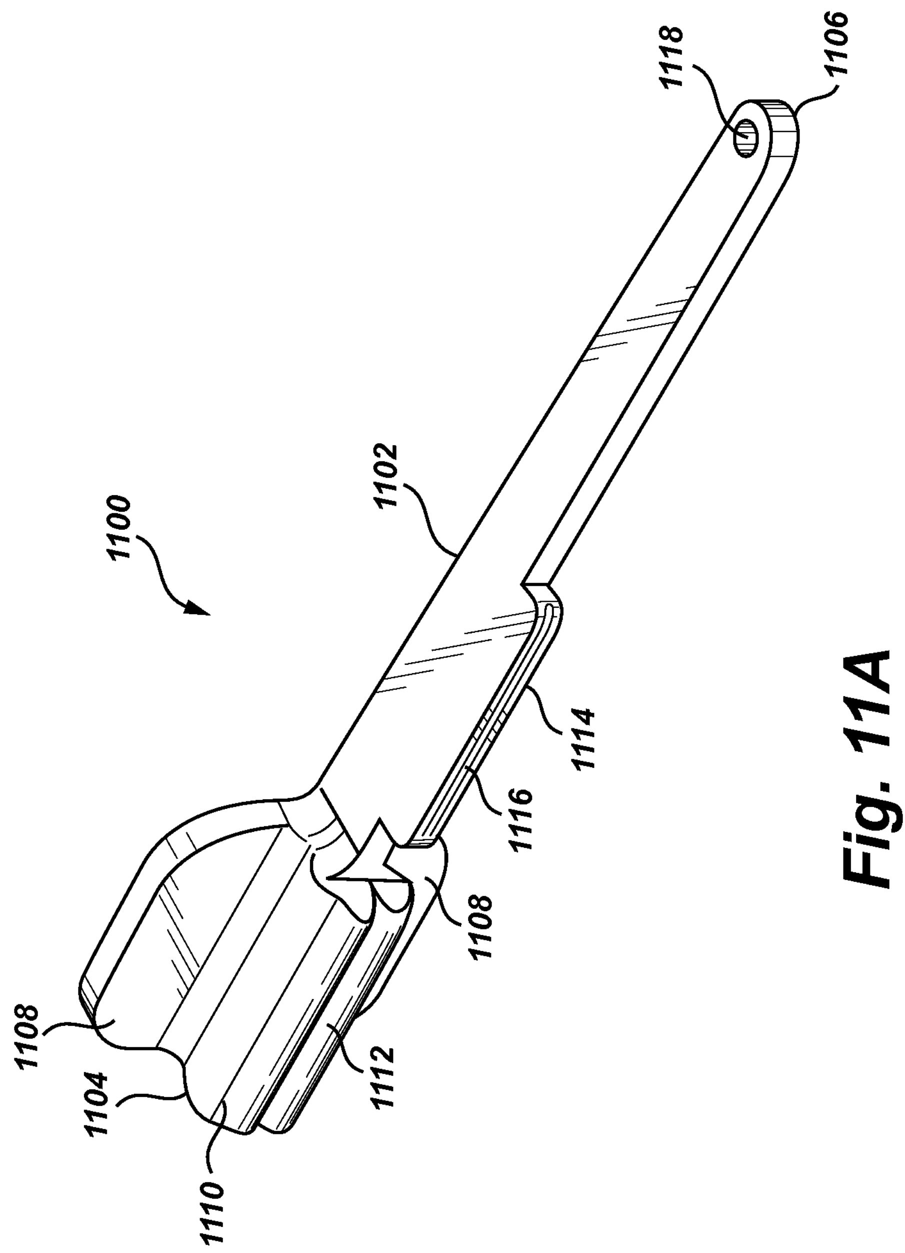
FIGS. 11A-11D show various views of an exemplary stylet retainer according to principles described herein.
Figure 11B:
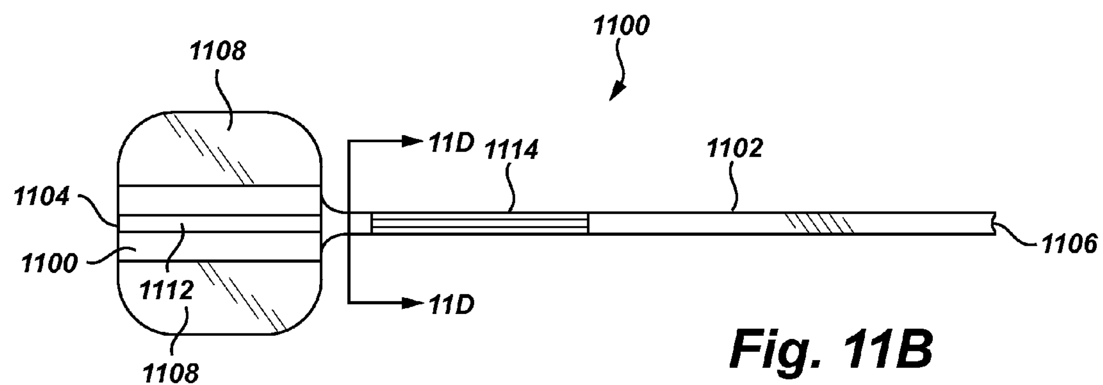
Figure 11C:
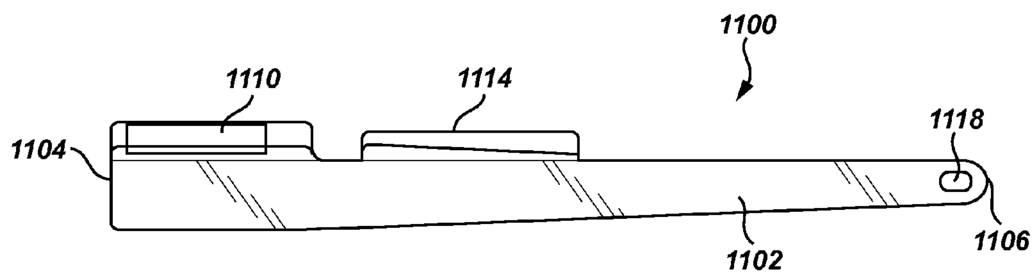
Figure 11D:
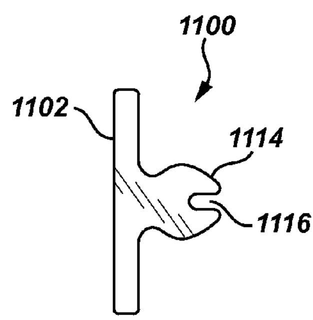

FIG. 11A is a perspective view of an exemplary stylet retainer 1100 that may be used to retain or stabilize stylet 400 within loading tool 700 while pre-curved electrode array 112 is loaded onto stylet 400. FIG. 11B is a cross-sectional bottom view of stylet retainer 1100, FIG. 11C is a cross-sectional side view of stylet retainer 1100, and FIG. 11D is a cross-sectional view of stylet retainer 1100 taken along the perspective line indicated in FIG. 11B. As will be described in more detail below, stylet retainer 1100 may be configured to couple to loading tool 700 to retain a proximal portion of stylet 400 within receptacle 710 of docking assembly 702 and a distal portion of stylet 400 within channel 716.

As shown in FIGS. 11A-11D, stylet retainer 1100 may include an elongated flange 1102 having a proximal end 1104 and a distal end 1106. Towards proximal end 1104, stylet retainer 1100 may include flanges 1108 perpendicularly extending away from elongated flange 1102. Flanges 1108 may be used by a surgeon or other user to handle stylet retainer 1100 (e.g., press stylet retainer 1100 down into position within loading tool 700 or remove stylet retainer 1100 from loading tool 700).

Stylet retainer 1100 may further include a retention member 1110 configured to facilitate removable coupling of a proximal portion of stylet retainer 1100 to docking assembly 702. Retention member 1110 may include a groove 1112 extending along a length thereof that is configured to fit over a portion of stylet 400 when stylet retainer 1100 is coupled to loading tool 700.

Stylet retainer 1100 may further include a backstop member 1114 extending perpendicularly away from elongated flange 1102. As will be described in more detail below, backstop member 1114 may be configured to prevent over-advancement of pre-curved electrode array 112 onto stylet 400. In some examples, backstop member 1114 may include a groove 1116 extending along its length that is configured to fit over a portion of stylet 400 when stylet retainer 1100 is coupled to loading tool 700.

Stylet retainer 1100 may further include a hole 1118 extending at least partially through a distal portion of elongated flange 1102. As will be described in more detail below, hole 1118 may be configured to facilitate removable coupling of the distal portion of stylet retainer 1100 to channel assembly 704.

Figure 12:
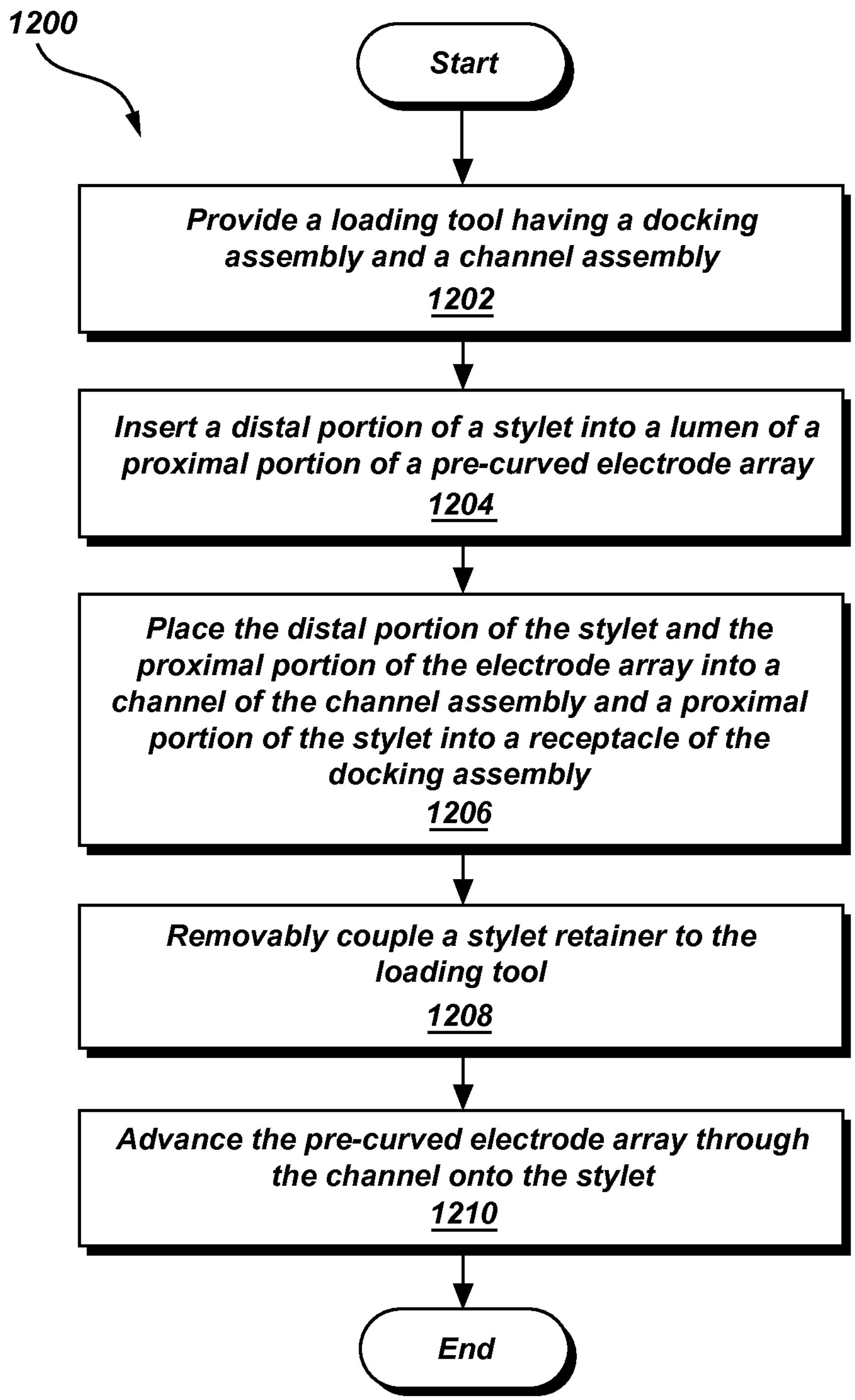
FIG. 12 illustrates an exemplary method of loading a pre-curved electrode array onto a stylet according to principles described herein.

FIG. 12 illustrates an exemplary method of loading a pre-curved electrode array onto a stylet. While FIG. 12 illustrates exemplary steps according to one embodiment, other embodiments may omit, add to, reorder, and/or modify any of the steps shown in FIG. 12.

In step 1202, a loading tool having a docking assembly and a channel assembly is provided. The loading tool may be similar to loading tool 700 and/or loading tool 800. As described above, the docking assembly may include a plurality of wing members that form a receptacle and the channel assembly may include a channel.

Figure 13A:
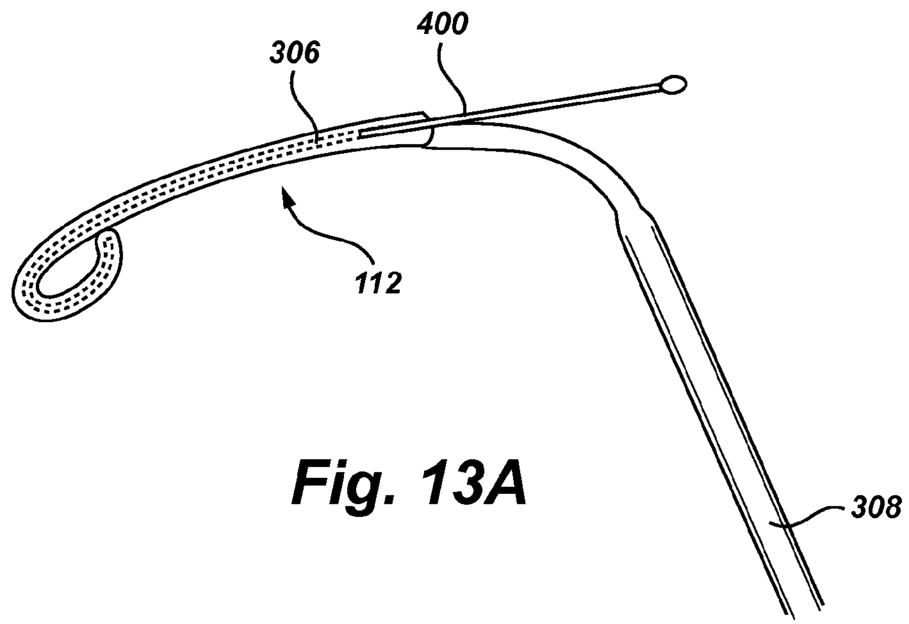
FIG. 13A shows a distal portion of a stylet inserted into a lumen of a proximal portion of a pre-curved electrode array according to principles described herein.

In step 1204, a distal portion of a stylet is inserted into a lumen of a proximal portion of a pre-curved electrode array. For example, FIG. 13A shows a distal portion of stylet 400 inserted into lumen 306 of proximal portion of pre-curved electrode array 112. In some examples, as shown in FIG. 13A, the proximal portion of pre-curved electrode array 112 into which stylet 400 is inserted is relatively straight.

Figure 13B:
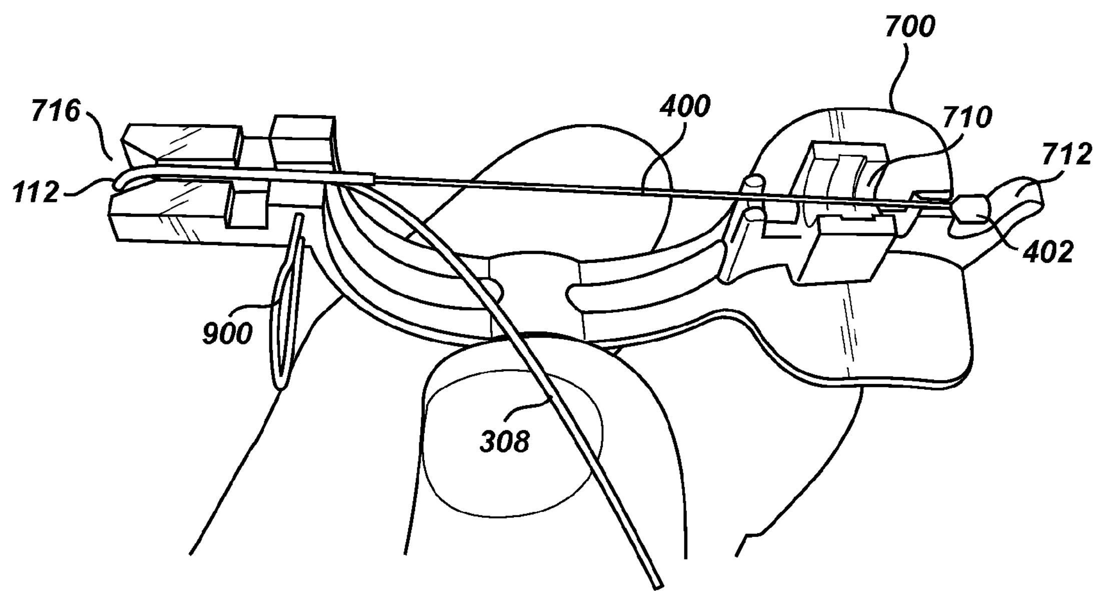
FIG. 13B shows a loading tool after a stylet has been placed therein according to principles described herein.

In step 1206, the distal portion of the stylet and the proximal portion of the electrode array are placed into the channel the of channel assembly and a proximal portion of the stylet is placed into a receptacle of the docking assembly. For example, FIG. 13B shows loading tool 700 after stylet 400 has been placed therein. As shown in FIG. 13B, a proximal portion of stylet 400 is located within receptacle 710 and a distal portion of stylet 400 is located within channel 716. Pre-curved electrode array 112 is also located within channel 716. At this point, as shown in FIG. 13B, retainer clip 900 is disengaged.

As shown in FIG. 13B, handle member 402 of stylet 400 may be aligned with backstop member 712 in order to facilitate proper placement of stylet 400 within receptacle 710. Any other means of facilitating proper placement of stylet 400 within receptacle 710 may be used as may serve a particular application.

Figure 13C:
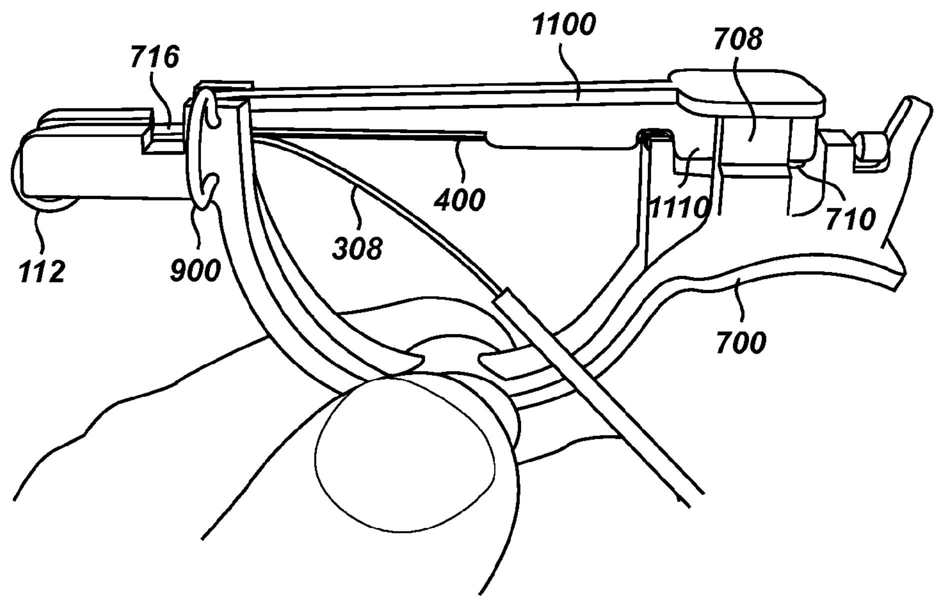
FIG. 13C shows a stylet retainer removably coupled to a loading tool according to principles described herein.

In step 1208, a stylet retainer is removably coupled to the loading tool. For example, FIG. 13C shows stylet retainer 1100 removably coupled to loading tool 700. As shown in FIG. 13C, stylet retainer 1100 may be configured to at least partially cover receptacle 710 and channel 716, thereby retaining stylet 400 therein.

In some examples, at least a subset of wing members 708 are configured to apply a retaining force against a proximal portion of stylet retainer 1100, thereby facilitating removable coupling of stylet retainer 1100 to docking assembly 702. For example, one or more wing members 708 may apply a retaining force to retention member 1110 of stylet retainer 1100.

Stylet retainer 1100 may be removably coupled to channel assembly 704 by engaging retaining clip 900 after stylet retainer 1100 has been placed such that it at least partially covers channel 716. For example, hole 1118 of stylet retainer 1100 may be aligned with at least one of holes 720 of channel assembly 704. Retaining clip 900 may then be inserted into hole 1118 and at least one of holes 720, thereby coupling stylet retainer 1100 to channel assembly 704.

Figure 13D:
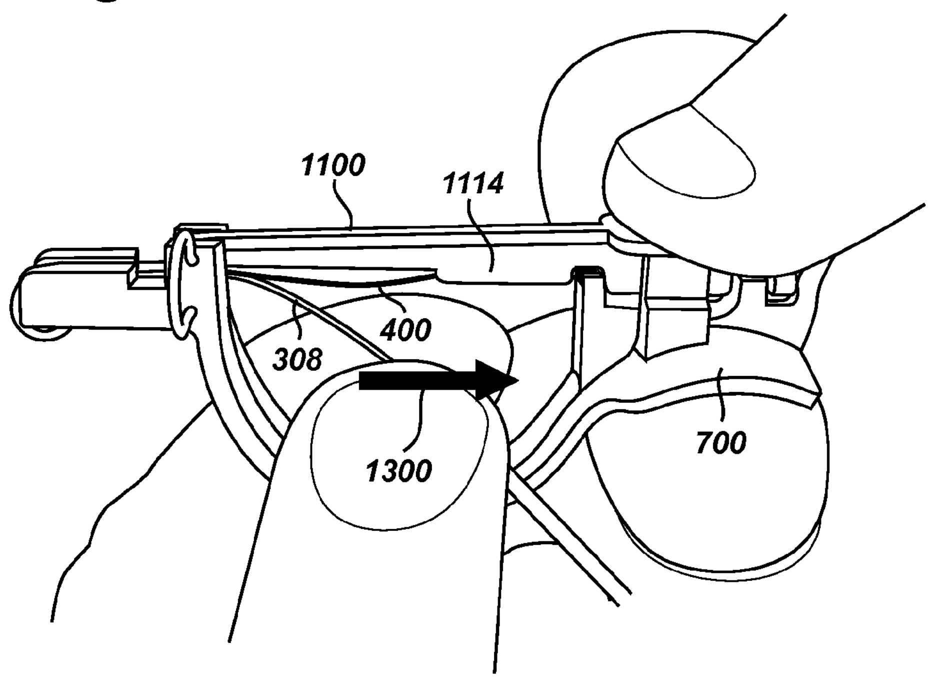
FIG. 13D illustrates how a pre-curved electrode array may be loaded onto a stylet according to principles described herein.

In step 1210, the pre-curved electrode array is advanced through the channel and onto the stylet. For example, once stylet 400 has been secured within channel 716, a surgeon or other user may load electrode array 112 onto stylet 400 by pulling lead body 308 of electrode array 112 in a direction indicated by arrow 1300 shown in FIG. 13D. As lead body 308 is pulled, the pre-curved portion of electrode array 112 enters channel 716 and is loaded onto stylet 400. In some examples, lead body 308 may be pulled until it comes in contact with backstop member 1114. When lead body 308 comes in contact with backstop member 1114, a surgeon or other user may know that electrode array 112 is fully loaded onto stylet 400.

After pre-curved electrode array 112 is loaded onto stylet 400, stylet 400 may be removed from loading tool 700. To this end, stylet retainer 1100 may be disengaged from loading tool 700 by disengaging retainer clip 900 and applying an upward force against flanges 1108 of stylet retainer 1100. It will be recognized that stylet retainer 1100 may be removed in any other way as may serve a particular application.

Figure 13E:
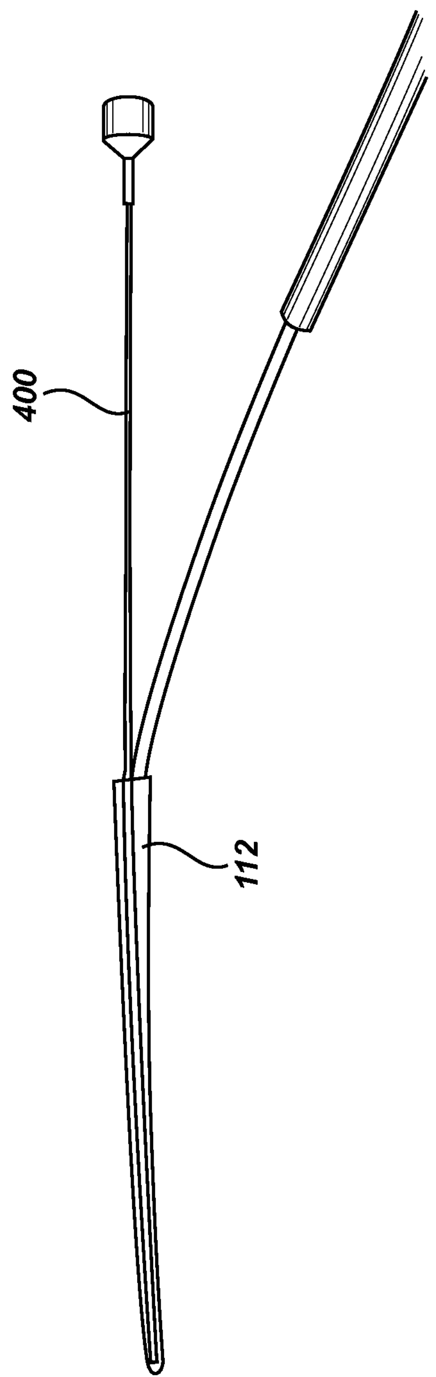
FIG. 13E shows a pre-curved electrode array and a stylet after the stylet has been removed from a loading tool according to principles described herein.

FIG. 13E shows electrode array 112 and stylet 400 after stylet 400 has been removed from loading tool 700. As shown in FIG. 13E, pre-curved electrode array 112 has been loaded onto stylet 400 and may now be inserted into a duct of a cochlea using any suitable insertion technique.

In some examples, pre-curved electrode array 112 may be inserted into a duct of the cochlea in accordance with an off stylet insertion technique. As used herein, an “off stylet insertion technique” comprises any technique used to insert pre-curved electrode array 112 into a duct of the cochlea that, at least during a portion of the insertion process, does not employ the use of an insertion tool coupled to stylet 400. For example, only the stylet 400 may be used to initially insert pre-curved electrode array 112 at least partially into the cochlea. At some point, forceps or some other tool may be used to advance the pre-curved electrode array 112 all the way into the cochlea while holding stylet 400 in a stationary position with respect to the cochlea. Alternatively, the pre-curved electrode array 112 may be entirely inserted into the cochlea using only the stylet 400. In other words, with stylet 400 fully inserted within pre-curved electrode array 112, pre-curved electrode array 112 may be inserted into the cochlea to its final implant depth without the use of an insertion tool coupled to stylet 400. It will be recognized that other off stylet insertion techniques may be used in accordance with the systems and methods described herein. It will also be recognized that any other insertion technique other than an off stylet insertion technique may be used in accordance with the systems and methods described herein.

Figure 14:
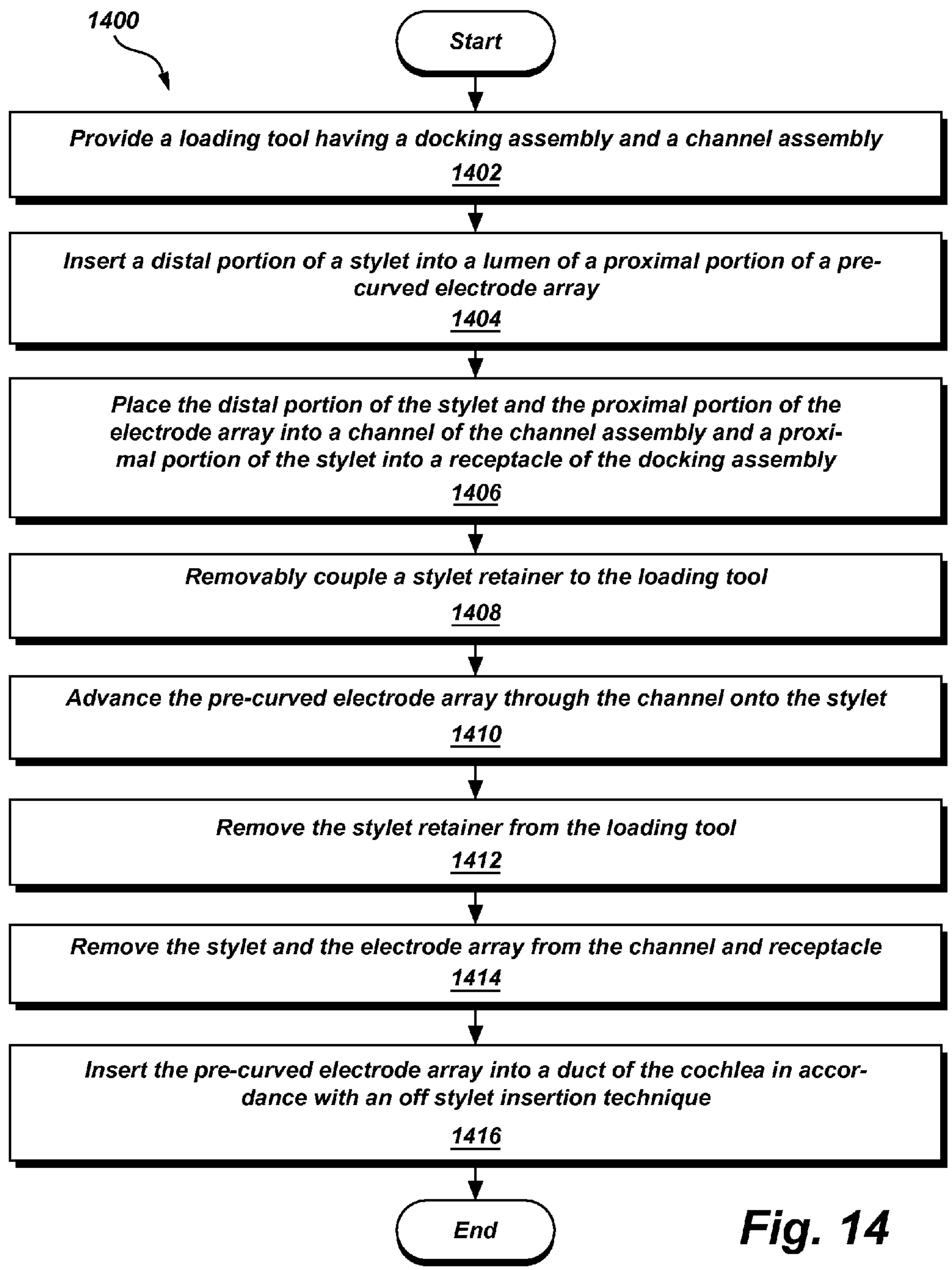
FIG. 14 illustrates an exemplary method of implanting a pre-curved electrode array into a duct of a cochlea according to principles described herein.

FIG. 14 illustrates an exemplary method of implanting a pre-curved electrode array into a duct of a cochlea. While FIG. 14 illustrates exemplary steps according to one embodiment, other embodiments may omit, add to, reorder, and/or modify any of the steps shown in FIG. 14.

In step 1402, a loading tool having a docking assembly and a channel assembly is provided. The loading tool may be similar to loading tool 700 and/or loading tool 800. As described above, the docking assembly may include a plurality of wing members that form a receptacle and the channel assembly may include a channel.

In step 1404, a distal portion of a stylet is inserted into a lumen of a proximal portion of a pre-curved electrode array. The distal portion of the stylet may be inserted into the lumen in any of the ways described herein.

In step 1406, the distal portion of the stylet and the proximal portion of the electrode array are placed into the channel of channel assembly and a proximal portion of the stylet is placed into a receptacle of the docking assembly.

In step 1408, a stylet retainer is removably coupled to the loading tool. The stylet retainer may be removably coupled to the loading tool in any of the ways described herein.

In step 1410, the pre-curved electrode array is advanced through the channel and onto the stylet. The pre-curved electrode array may be advanced onto the stylet in any of the ways described herein.

In step 1412, the stylet retainer is removed from the loading tool. The stylet retainer may be removed in any of the ways described herein.

In step 1414, the stylet and electrode array are removed from the channel and from the receptacle. The stylet and electrode array may be removed in any of the ways described herein.

In step 1416, the pre-curved array is inserted into a duct of the cochlea in accordance with an off stylet insertion technique.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
a stylet;
a loading tool comprising
a docking assembly comprising a plurality of wing members that form a receptacle that receives a proximal portion of a stylet,
a channel assembly comprising a channel that receives and allows passage therethrough of a pre-curved electrode array, wherein said channel further receives a distal portion of said stylet, and
a connecting member that connects said channel assembly to said docking assembly; and
a stylet retainer that removably couples to said loading tool, wherein, while said stylet retainer is removably coupled to said loading tool, said stylet retainer retains said proximal portion of said stylet within said receptacle and said distal portion of said stylet within said channel.

2. The system of claim 1, wherein said stylet retainer stabilizes said stylet within said loading tool while said pre-curved electrode array is loaded onto said stylet and while said stylet retainer is removably coupled to said loading tool.

3. The system of claim 1, wherein said stylet retainer at least partially covers said channel and said receptacle while said stylet retainer is removably coupled to said loading tool.

4. The system of claim 1, wherein a proximal portion of said stylet retainer is configured to be removably coupled to said docking assembly and wherein a distal portion of said stylet retainer is configured to be removably coupled to said channel assembly.

5. The system of claim 4, wherein at least a subset of said wing members apply a retaining force against said proximal portion of said stylet retainer while said stylet retainer is removably coupled to said loading tool, said retaining force facilitating said removable coupling of said proximal portion of said stylet retainer to said docking assembly.

6. The system of claim 4, further comprising a retainer clip configured to be inserted within said channel assembly to facilitate said removable coupling of said distal portion of said stylet retainer to said channel assembly.

7. The system of claim 6, wherein said distal portion of said stylet retainer comprises a hole extending at least partially therethrough, said hole configured to receive said retainer clip.

8. The system of claim 1, wherein said stylet retainer comprises a backstop flange that prevents over-advancement of said pre-curved electrode onto said stylet.

9. The system of claim 1, wherein said docking assembly comprises one or more flanges that facilitate handling of said loading tool.

10. The system of claim 1, wherein said connecting member comprises a c-shaped connecting member.

11. The system of claim 1, wherein said connecting member comprises a finger grip.

12. The system of claim 1, wherein said channel assembly further comprises one or more wall members that prevent said pre-curved electrode array from moving laterally within said channel.

13. The system of claim 1, wherein said loading tool is made out of a single mold.

* * * * *